United States Patent [19]

Felix et al.

[11] Patent Number: 4,965,343

[45] Date of Patent: Oct. 23, 1990

[54] METHOD OF PEPTIDE SYNTHESIS

[75] Inventors: Arthur M. Felix, West Caldwell, N.J.; Alain Fournier, Pierrefonds, Canada; Waleed Danho, Wayne, N.J.

[73] Assignee: Hoffmann-La Roche Inc., Nutley, N.J.

[21] Appl. No.: 149,261

[22] Filed: Jan. 28, 1988

[51] Int. Cl.$^5$ .......................... C07K 1/02; C07K 1/04; C07K 7/06
[52] U.S. Cl. .................... 530/334; 530/333; 530/336; 530/327; 530/328
[58] Field of Search .................. 530/334, 336

[56] References Cited

U.S. PATENT DOCUMENTS 4,769,445  9/1988  Constoch et al. ............. 530/333

FOREIGN PATENT DOCUMENTS 0161468    11/1985  European Pat. Off. ........... 530/334
81400976.7 12/1987  European Pat. Off. .

OTHER PUBLICATIONS

Fourrier, A. et al., Int. J. Peptide Protein Res., 33: 133–139, 1989.
The Proteins, vol. II, 3rd ed., Ed.; Neurath, Hill, Boeder, Academic Press, 1976.
Fournier, A., et al., Int. J. Peptide Protein Res. 31: 86–97, 1988.
Felix, A., et al., Int. J. Peptide Protein Res. 31: 231–238, 1988.
Le Nguyen, D., et al., Peptide Chemistry, 1987, 231–238, T. Shiba & S.Sakakibara (Editors), pub. 1988.
Penke, B., et al., J. Org. Chem., 52: 1197–1200, 1987.
Penke, B., et al., J. Med. Chem., 27: 845–894, 1984.
Le Nguyen, D., J. Chem. Soc. Penkin Trans. I: 1915–1919, 1987.
Casto, B., et al., Tett. Lett., 14: 1219–1222, 1975.
Pluslec, T., J. Med. Chem., 13; 349–352, 1970.
Toth, G., et al., Int. J. Peptide Protein Res., 26: 630–638, 1985.
Castro, et al., Pept., Proc. Eur. Pept. Symp., 13th, 1974, Nolman, Yechesnel (Ed.), pub. 1975.
Ondetti, M., JACS, 92: 195–199, 1970.
Castro, Journal of the Chemical Society, Perkin Translation, I., 1025 (1985).
Rivaile, Tetrahedron, 36, 3143 (1980).
Audousset-Puech et al., FEBS Letters, 200: 181 (1986).

Primary Examiner—Howard E. Schain
Assistant Examiner—Susan Perkins
Attorney, Agent, or Firm—George M. Gould; William H. Epstein; John J. Schlager

[57] ABSTRACT

A method for the solid phase synthesis of multi-sulfated peptides comprising coupling side-chain unprotected hydroxyamino acids to the peptide chain utilizing benzotriazol-1-yl-oxy-tris (dimethyl)-phosphonium hexafluorophosphate (BOP) as a coupling reagent.

19 Claims, No Drawings

METHOD OF PEPTIDE SYNTHESIS

BACKGROUND OF THE INVENTION

This invention is directed to a process for the preparation of peptides and peptide amides which contain sulfated tyrosine or sulfated hydroxy amino acids using benzotriazol-1-yl-oxy-tris (dimethyl)-phosphonium hexafluoro-phosphate (BOP) as a coupling reagent. In the method of the invention the need to use amino acid protecting groups to preclude unwanted side reactions during peptide synthesis is minimized. The instant invention is particularly directed to the solid phase synthesis of potent CCK-8 analogs using BOP as a coupling reagent.

Cholecystokinin (CCK) is a polypeptide hormone which was first isolated as a 33-amino acid peptide from the porcine gastrointestinal tract. [Mutt et al., Biochem. J. 125. 57-58 (1971) and Mutt et al., Clin. Endocrinol. supplement, 5, 175-183 (1976)]. Peripherally administered CCK has been shown to produce satiety in the rat and the monkey and infusions of CCK-8, the octapeptide analog of CCK, has been shown to decrease food intake in lean and obese men. G.P. Smith, Int. J. Obesity 8 Suppl. 1:35-38 (1984); Jorpes et al., Acta. Chem. Scand. 18:2408 (1964); Della-Fera et al., Science 206:471-73 (1979); Gibbs et al., J. Comp. Physiology and Psychology 84, 488-495 (1973). It is now accepted that CCK has satiety-inducing effects and thus, may be useful to reduce or suppress food intake in man.

The polypeptide hormone, CCK-33, has the amino acid sequence:
Lys-Ala-Pro-Ser-Gly-Arg-Val-Ser-Met-Ile-Lys-Asn-Leu-Gln-Ser-Leu-Asp-Pro-Ser-HisArg-Ile-Ser-Asp-Arg-Asp-Tyr-($SO_3H$)-Met-Gly-TrpMet-Asp-Phe-$NH_2$.

Fragments of CCK, e.g. CCK-8 and CCK-7 also have been shown to have satiety-inducing effects. CCK-8 has the amino acid sequence:

Asp-Tyr-($SO_3H$)-Met-Gly-Trp-Met-Asp-Phe-$NH_2$

CCK-7 is one amino acid less than CCK-8, i.e., it is CCK-8 minus the 26-position Asp.

Ondetti and Pluscec [J. Am. Chem. Soc. 92. 195 (1970); J. Med Chem. 13, 349 (1970); see also U.S. Patent Nos. 3,723,406; 3,778,429; 3,835,315 and 3,892,726], synthesized CCK-8 and a series of analogs by the method of solution phase peptide synthesis. Toth and Kovacs [Int. J. Peptide Protein Res. 26, 630 (1985)]evaluated four different strategies for preparing CCK-8 peptides using solution phase synthesis. Penke et al. (U.S. Pat. No. 4,102,878) described a process whereby CCK-8 was produced by the known method of solution phase peptide chemistry through an improved sulfation procedure using pyridinium acetyl sulfate (PAS) as the sulfation agent. Penke and Rivier [J. Med Chem. 27. 845 (1984)]described the synthesis of unsulfated analogs of CCK-8 using solid phase peptide methodology by the standard procedure generally described by Merrifield [J. Am. Chem. Soc. 85, 2149 (1963)]. The non-sulfated heptapeptide analogs were synthesized on methylbenzhydrylamine-resin with t-butyloxyCarbonyl (Boc) protected amino acids. The beta carboxy group ($\beta$-COOH) of the amino acid of Asp was protected with 0-Benzyl, and the hydroxy group of Ser, Thr, Hyp was protected with the benzyl group. The phenolic group of the amino acid Tyr was protected with the 2,6-dichlorobenzyl group. Other amino acid side chains were unprotected. Each coupling was made with dicyclohexyl-carbodimide (DCC). N-terminal acetylation was performed on the resin using acetic anhydride. The peptides were cleaved from the resin with hydrogen fluoride in the presence of scavengers, purified by high performance liquid chromatography (HPLC) and sulfated with PAS.

Comstock and Rosamond in European Patent 161468 described the solid phase synthesis of peptides containing sulphated tyrosine by (a) preparing a peptidyl derivative of an aminomethyl polystyrene resin by attachment of a 4-($ROCH_2$)Phenylacyl group (R=acyl derived from protected amino acid) followed by sequential addition of active esters of protected amino acids; (b) converting tyrosine groups in the peptidyl resin to their sulfate esters by reaction with pyridine sulfur trioxide complex or (PAS); (c) cleaving the peptide from the resin by treatment with alkali, $NH_3$, aliphatic amines, or hydrazine. Penke and Rivier [J. Org. Chem. 52, 1197-1200 (1987)]described a new route for the synthesis of CCK-8 and analogs utilizing 2,4-dimethoxybenzhydrylamine support in conjunction with the fluoroylmethyloxy carbonyl tert-Butyl (Fmoc/tBu) strategy with trifluoroacetic acid as a cleavage reagent for removal of the peptide from the resin.

All the above mentioned processes utilize DCC, DCC/HOBt or symmetrical anhydride as the coupling reagents, however these reagents are not without shortcomings [Bodanszky (1984), Principles of Peptide Synthesis, Springer Verlag, New York], and side-reactions such as racemization or intramolecular rearrangement. Repetitive couplings are often required for the complete introduction of a residue in the peptide chain during the synthesis. Among several coupling reagents suggested for replacement of DCC, the "BOP reagent" [benzotriazol-1-yl-oxytris(dimethylamino)phosphonium hexafluoro-phosphate] proposed by Castro, Tet. Lett., 14 1219-1222, (1975) represents an attractive alternative. This is a non-hygroscopic salt, very stable and soluble in the usual organic solvents used in peptide synthesis. The activation of the carboxy (COOH) function is reported to proceed via the formation of an acyloxyphosphonium derivative, subsequently transformed into the HOBt active ester, which undergoes rapid coupling with the growing peptide chain.

The BOP reagent has been used in solution synthesis [Castro, J. Chem. Soc. Perkin Trans. I, 1025-1031 (1985)] and has been applied/in solid phase for fragment coupling [Rivaille, Tet. 36, 3413-3419 (1980)]and stepwise synthesis [Martinez, FEBS Lett. 200, 181-185 (1986)]. However, the BOP reagent has always been used in solid phase synthesis in conjunction with fully protected trifunctional amino acids. The process described in this invention utilizes the BOP reagent for the solid phase coupling of unprotected aliphatic and aromatic hydroxyamino acids.

SUMMARY OF THE INVENTION

The instant invention comprises a method for the solid phase synthesis of multi-sulfated peptides by coupling side-chain unprotected hydroxyamino acids to the peptide chain with BOP.

Preferred is where the method of the invention is used to synthesize CCK or analogs thereof.

Definitions

The following abbreviations or symbols are used to represent amino acids, active groups, protecting group and the like.

BOP - Benzotriazol-1-yl-oxy-tris-(dimethylamino)-phosphonium hexafluoro-phosphate OCH$_2$PAM resin - [4-(oxymethyl)-phenylacetamidomethyl]-polystyrene resin PAS - Pyridinium acetyl sulfate PS - Pyridine sulfur trioxide complex BOP-Cl - Bis-(2-oxo-3-oxazolidinyl) phosphinic chloride Aeg - Aminoethylglycine Amino acids are given their commonly understood three letter designation. The L-isomer is meant unless otherwise specified.

DETAILED DESCRIPTION

The invention comprises the solid phase synthesis of multi-sulfated peptides utilizing BOP to couple side chain unprotected hydroxyamino acids.

Preferred is the solid phase synthesis of CCK peptides and analogs thereof utilizing BOP to couple side-chain unprotected hydroxyamino acids.

Particularly preferred is the solid phase synthesis of a peptide of the following formula utilizing BOP to couple side chain unprotected hydroxyamino acids.

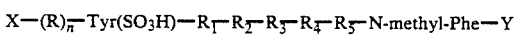

$$X-(R)_{\overline{n}}-Tyr(SO_3H)-R_{\overline{1}}-R_{\overline{2}}-R_{\overline{3}}-R_{\overline{4}}-R_{\overline{5}}-N\text{-methyl-Phe}-Y$$

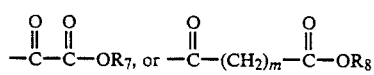

wherein $X = \overset{O}{\underset{\|}{C}}-R_6,\ \overset{O}{\underset{\|}{C}}-OR_6,\ \overset{O}{\underset{\|}{-C}}-(CH_2)_m-CH_3$, $$-\overset{O}{\underset{\|}{C}}-\overset{O}{\underset{\|}{C}}-OR_7,\ \text{or}\ -\overset{O}{\underset{\|}{C}}-(CH_2)_m-\overset{O}{\underset{\|}{C}}-OR_8$$

R = Asp, Aeg
$R_1$ = Met, Nle, Leu, or 0 (Zero)
$R_2$ = Gly, Ala, D-Ala, or β-Ala
$R_3$ = Trp, Trp (For)
$R_4$ = Met, Nle, Nva, Pro
$R_5$ = Thr(SO$_3$H), Ser(SO$_3$H), or Hyp(SO$_3$H)
$R_6$ = H, C$_{1-3}$alkyl
$R_7$ = $R_8$ = H, C$_{1-3}$alkyl, or C$_{1-3}$haloalkyl
$R_8$ = H, C$_{1-3}$alkyl
Y = OR$_8$ or NR$_9$R$_{10}$
$R_9$ = H, C$_{1-3}$alkyl
$R_{10}$ = H, C$_{1-3}$alkyl
n = 0 or 1
m = 1-14

Particularly preferred is where the above method is utilized to synthesize peptides of the following formulas:

(b) sequential addition of side-chain unprotected t-butyloxycarbonyl (Boc) hydroxyamino acid using the BOP reagent. In general, single couplings and 3 equivalents of BOP and three equivalents of Boc amino acids are used.

(c) reaction of the hydroxyl groups with sulfating agent (PAS) or pyridine sulfur trioxide complex at elevated temperature (40–50°C.) to provide the sulfate esters.

(d) cleavage of the multi-sulfated peptide with a nucleophilic agent selected from the group consisting of ammonia, amines or hydrazine.

(e) single step purification of the multi-sulfated peptide by semi-preparative HPLC.

Preparation of Peptides of Invention

The peptides of the invention were prepared using solid phase synthesis by the method generally described by Merrifield [J. Am. Chem. Soc. 85, 2149 (1963)]. Solid phase synthesis is commenced from the C-terminal end of the peptide by coupling a protected amino acid by an amide bond to a suitable resin, e.g. phenylacetamidomethyl (PAM) resin. Boc-amino acid-OCH$_2$-PAM resin supports are commercially available and generally used for peptide synthesis.

All solvents used in the preparations described herein, e.g. methylene chloride (CH$_2$Cl$_2$), 2-propanol, dimethylsulfide (DMS), and dimethylforamide (DMF) were Burdick and Jackson "Distilled in Glass" grade and used without further purification. Trifluoroacetic acid (TFA), diisopropYlethylamine (DIEA), and (BOP) were purchased from Chemical Dynamics Corp. and were "sequanal" grade purity. 1,2-ethanedithiol (EDT) was purchased from Sigma Chemical Co. and used without further purification. All α-amino protected amino acids were of the L-configuration unless otherwise indicated and were obtained from Bachem.

The following instrumentation was utilized. Thin layer chromatography (TLC) was performed on glass backed precoated silica gel 60 F254 plates (Merck) using appropriate solvent systems. Detection of spots was by UV fluoroscence quenching (254 nm absorption), iodine staining, or ninhydrin spray (for primary and secondary amines).

For amino acid analyses, peptides were hydrolyzed in 6N HCl containing phenol at 115°C. for 24 hours in evacuated Reacti-Therm hydrolysis tubes. Analyses were performed on a Beckman 121M amino acid analyzer.

HPLC was conducted on a LDC apparatus consisting of a Constametric I pump, a Constametric III pump, a Gradient Master solvent programmer and mixer, and a Spectromonitor III variable wavelength UV detector.

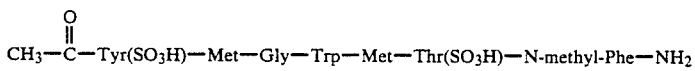

$$CH_3-\overset{O}{\underset{\|}{C}}-Tyr(SO_3H)-Met-Gly-Trp-Met-Thr(SO_3H)-N\text{-methyl-Phe}-NH_2$$

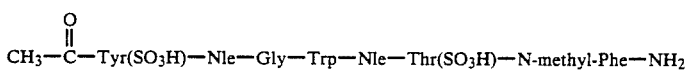

$$CH_3-\overset{O}{\underset{\|}{C}}-Tyr(SO_3H)-Nle-Gly-Trp-Nle-Thr(SO_3H)-N\text{-methyl-Phe}-NH_2$$

This invention provides a general process for the solid phase synthesis of multi-sulfated peptides containing tyrosine and hydroxyamino acids using the BOP reagent and minimal side-chain protection. The process is comprised of the following steps:

(a) preparation of the α-amino acid protected O-CH$_2$-PAM-resin according to known methods.

Analytical HPLC chromatography was performed on reversed phase with Waters Micro Bondapak C$_{18}$ columns (0.4 ×25 cm). Preparative HPLC separations were run on (2.5 ×50 cm) Partisil M20 10/50 ODS-3 column, or (2.3×30 cm) micro Bondapak C$_{18}$ column; in both cases, a pre-column of Whatman Co-Pell ODS pellicular packing was used.

The peptides were assembled in a stepwise manner on a solid support using a manual "shaker in the round" from Glas-Col Apparatus Co., Terre Haute, IN). Boc-Phe-OCH$_2$-PAM resin was purchased from Vega Biotechnologies Inc., Tucson, AZ. Boc-N-methyl-Phe-O-CH$_2$-PAM resin was prepared according to the procedure of Mitchell et al. (J. Am. Chem. Soc.) 98, 7357 (1976).

The initial synthesis was started with Boc-amino acid-0-CH$_2$—PAM resin. The protocol for a typical synthetic cycle was as follows:

| Step | Reagent | Time |
|---|---|---|
| 1 | 1% DMS/CH$_2$Cl$_2$ | 1 × 1 min |
| 2 | 50% TFA/CH$_2$Cl$_2$ + 1% DMS (v/v) | 1 × 1 min |
| 3 | 1% DMS/CH$_2$Cl$_2$ | 1 × 1 min |
| 4 | 50% TFA/CH$_2$Cl$_2$ + 1% DMS (v/v) | 1 × 20 min |
| 5 | CH$_2$Cl$_2$ | 4 × 1 min |
| 6 | 10% DIEA/CH$_2$Cl$_2$ | 1 × 5 min |
| 7 | CH$_2$Cl$_2$ | 1 × 1 min |
| 8 | 10% DIEA/CH$_2$Cl$_2$ | 1 × 5 min |
| 9 | CH$_2$Cl$_2$ | 1 × 1 min |
| 10 | MeOH | 2 × 1 min |
| 11 | CH$_2$Cl$_2$ | 1 × 1 min |
| 12 | DMF | 2 × 1 min |
| 13 | 3 eq. Boc-amino acid COOH/DMF + 3 eq. BOP reagent/DMF + 6 eq. DIEA | 1 × 120 min |
| 14 | DMF | 2 × 1 min |
| 15 | MeOH | 2 × 1 min |
| 16 | CH$_2$Cl$_2$ | 3 × 1 min |

Solvents for all washings and couplings were measured to volumes of 10–20 mL/g resin. Coupling reactions were monitored by the Kaiser ninhydrin test (after step 16) to determine whether each coupling was complete. [Kaiser et al., Anal. Biochem. 34, 595–598 (1970)].

The fully assembled peptide-resin was disulfated using pyridinium acetyl sulfate (PAS) or pyridine sulfur trioxide complex (PS). A typical sulfation is carried out as follows: PAS (1.09 g; 5.1 mmoles, 38 equiv.) is dissolved in 50 mL of dry pyridine and 0.5 g of peptide-resin (0.13 mmole of peptide) is added. The suspension is shaken 4 hours at 45°C. then filtered on a sintered glass funnel and successively washed with pyridine, DMF and MeOH. The resin is dried overnight in vacuo. Cleavage of the disulfate peptide from the resin was achieved as follows:

The dried peptide-resin is placed in a Wheaton pressure bottle (250 mL capacity). The container is purged with anhydrous ammonia, cooled to −78°C. using a dry ice-acetone bath, and ammonia (50 mL) condensed into the reaction vessel. The bottle is tightly capped, the bath is removed and the resin stirred at room temperature. At the end of the reaction, the pressure bottle is cooled to −78°C. before opening and the ammonia is evaporated quickly by immersing the vessel in a water bath. The peptide is extracted with MeOH. The solvent is evaporated to yield the crude peptide. Preparative purification was carried out directly on the crude peptide on an ES Industries C$_{18}$ (10$\mu$) column (1.25×30cm). The column was eluted at 5 mL/min with a solvent system consisting of (A) 0.01M ammonium acetate and (B) acetonitrile in a step gradient mode: 5 to 15% (B) 6 min, 15–45% (B) 2 hrs with detection at 280 nm. Fractions were collected at 2 min intervals and fraction pooling was determined by analytical HPLC using a Waters $\mu$Bondapak C$_{18}$ 10 $\mu$m column (0.39×30 cm), using a linear gradient of (A) acetonitrile and (B) 0.01M ammonium acetate (20–50% (B) 30 min); flow rate, 2 mL/min and detection at 225 nm. The purity and characterization of the sulfated peptides were determined by analytical HPLC, amino acid analysis, UV, IR, MS and NMR spectroscopy.

The present invention will be further described in connection with the following Examples which are set forth for the purposes of illustration only.

EXAMPLE 1

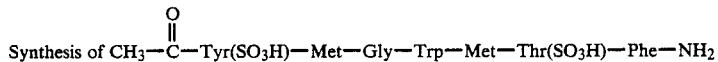

Synthesis of $CH_3-\overset{O}{\underset{\|}{C}}-Tyr(SO_3H)-Met-Gly-Trp-Met-Thr(SO_3H)-Phe-NH_2$ 1. Solid Phase Synthesis Boc-Phe-PAM resin (5 g; 1.8 mmole) is deprotected and neutralized according to the protocol described on page 9 (Steps 1–8). After washing (Steps 9–12), the coupling (Step 13) is carried out with 3 equivalents of Boc-Thr (1.18 g; 5.4 mmoles) and BOP reagent (2.39 g; 5.4 mmoles), each one separately dissolved in 25 mL of DMF, are introduced into the reactor. To that resin suspension is added 1.89 mL (10.8 mmoles) of DIEA and the reaction is carried out for 2 hours at room temperature. After the coupling, the resin is washed (Steps 14–16) and is then ready for the next coupling cycle. The subsequent residues to be linked to the growing peptide chain are: Boc-Met (1.35 g); Boc-Trp (1.64 g); Boc-Gly (0.94 g); Boc-Met (1.35 g) and Boc-Tyr (1.52 g). The same procedure is used in each case. After the incorporation of the last Boc-amino acid (Boc-Tyr), the peptide resin goes through a final deprotection-neutralization cycle (Steps 1–12) and the free amino group is acetylated using 3 equivalents of acetic acid (324 mg; 310 $\mu$L) and BOP reagent in the presence of 6 equiv. DIEA, according to the same protocol as used previously for the Boc-amino acid residues.

2. Solid Phase Disulfation Procedure

The sulfate ester-containing peptide is prepared by disulfation of the side-chain of Tyr and Thr using (PAS) or pyridine sulfur trioxide complex (PS). A typical sulfation is carried out as follows: PAS (218 mg; 1 mmol, 38 equiv.) or PS (162 mg; 1 mmole, 38 equiv.) is dissolved in 20 mL of dry pyridine and 100 mg of peptide-resin ( 0.0268 mmole of peptide) is added. The suspension is shaken 4 hours at 45° C then filtered on a sintered glass funnel and successively washed with pyridine, DMF and MeOH. The resin is dried overnight in vacuo.

3. Ammonolysis of the Peptide-resin

The dried peptide-resin is placed in a Wheaton pressure bottle (250 mL capacity). The container is purged with anhydrous ammonia, cooled to −78°C. using a dry ice-acetone bath, the ammonia (20 mL) condensed into the reaction vessel. The bottle is tightly capped, the bath is removed and the resin stirred overnight at room temperature. At the end of the reaction, the pressure bottle is cooled to −78°C. before opening and the ammonia is evaporated quickly by immersing the vessel in a water bath. The peptide is extracted with MeOH (3×15 mL). The solvent is evaporated and the crude N-aCetyl CCK-8 analog is ready for purification. From 100 mg of sulfated peptide resin, 27.2 mg of crude material was obtained after ammonolysis. Analysis by HPLC indicated that the sample o contained 14.3 mg of disulfated peptide for an overall yield of 50%.

4. Purification and Characterization of the Crude Peptide

An 8.2 mg portion was dissolved in 1 mL H$_2$O, centrifuged and filtered through a 0.45 µ Type HA Millipore filter. The filtrate was applied onto an ES Industries C$_{18}$ 10 µm column (1.25×30 cm). The column was eluted at 5 mL/min with a solvent system consisting of (A) 0.01M ammonium acetate and (B) o acetonitrile in a step gradient mode: 5 to 15% (B) in 6 min, 15–45% (B) 2 hrs with detection at 280 nm. Fractions were collected at 2 min intervals and fraction pooling was determined by analytical HPLC using a Waters µBondapak C$_{18}$ 10 µm column (0.39×30 cm), a linear gradient of (A) 0.01M ammonium acetate and (B) acetonitrile (20–50% (B) in 30 min); flow rate, 2 mL/min and detection at 225 nm. Fractions 13–15 were pooled and lyophilized to give 2.2 mg (25% overall yield) of pure material. Amino acid analysis (6N HCl, 110° C, 22h): Thr, 0.95; Gly, 1.00; Met, 2.01; Tyr, 0.97; Phe, 1.02. Ultraviolet spectrum: λmax 272 and 278 nm (0.1N KOH). Infrared spectrum: confirms —OSO$_3$H with peaks at 1252–1232 and 1048 cm$^{-1}$ (KBr) NMR (400 MHz): confirms Tyr$^{27}$(SO$_3$H) and Thr$^{32}$(SO$_3$H) [d$_6$DMSO]. The homogeneity of the disulfated material was determined by analytical HPLC using a µBondapak C$_{18}$, 10 µ Waters column (0.30×30 cm) and using (A) H$_2$O(0.125% TFA)-(B) ACN(0.125% TFA) in a linear gradient (20% to 55% (B) in 25 min) with a flow rate of 2.5 mL/min and detection at 215 nm (0.2 AUFS).

The synthesis of CCK analogs where Nle is substituted for Met may be accomplished according to this methodology except that Nle is substituted for Met in the solid phase synthesis procedure.

EXAMPLE 2

Preparation of CH$_3$—C(=O)—Tyr(SO$_3$H)—Met—Gly—Trp—Met—Thr(SO$_3$H)—N-methyl-Phe—NH$_2$

1. Solid Phase Synthesis

Boc-N-methyl-Phe-PAM resin (1 g, 0.34 mmole) is deprotected and neutralized according to the protocol described on page 9 (Steps 1–8). After washing (Steps 9–12) the coupling (Step 13) of Boc-Thr(tBu)-OH (0.275 g, 1.0 mmole) was carried out using BOP-Cl (0.254 g, 1.0 mmole) dissolved in CH$_2$Cl$_2$ in the presence of DIEA (0.350 mL, 2.0 mmole) for 45 min. starting with precooled CH$_2$Cl$_2$ at −20°C. and allowing it to warm to room temperature. After the coupling, the resin is washed (Step 14–16) and is ready for the next cycle. Boc-Thr (tBu)-N-methyl-Phe-PAM-resin is deprotected with 4N HCl/dioxane for 55 min. at room temperature washed twice with CH$_2$Cl$_2$, methanol, and CH$_2$Cl$_2$. The resin was suspended in 20 mL DMF and Boc-Met-OH (0.50 g, 2.0 mmole) which was preactivated with BOP (0.88 g, 2.0 mmole) in the presence of DIEA (700 µL, 4.0 mmole) in 5 mL of DMF was added in 0.5 mL increments over 90 min at room temperature. After the coupling the resin is washed (Step 14–16) as described in the protocol on page 9. At this point the loading of the peptide on the resin was reassessed by amino acid analysis (acid hydrolysis) and was found to be 0.14 mmole/g. The Boc-Met-Thr-N-methyl-Phe-PAM-resin is then deprotected and neutralized according to the protocol described on page 9 (Steps 1–8). After washing (Steps 9–12) the coupling (Step 13) is carried out with 3 equivalents of Boc-Trp-OH (304 mg, 1 mmole) and BOP reagent (425 mg, 1 mmole), each one separately dissolved in 5 mL of DMF, are introduced into the reactor. To that resin suspension is added 0.75 mL (4.3 mmole) DIEA and the reaction is carried our for 2 hours at room temperature. After the coupling the resin is washed (Steps 14–16) and is then ready for the next coupling cycle. The subsequent residues to be linked to the growing peptide chain are Boc-Gly-OH (175 mg. 1 mmole), Boc-Met-OH (250 mg, 1 mmole) and Boc-Tyr-OH (280 mg, 1 mmole). The same procedure is used in each case. After the incorporation of the last amino acid (Boc-Tyr), the peptide-resin goes through a final deprotection/neutralization cycle (Steps 1–12) and the free amino group is acetylated using 3 equivalents of acetic acid (324 mg, 310 mL) and BOP reagent in the presence of 6 equiv. DIEA according to the same protocol as used previously for the Boc-amino acid residues.

2. Solid Phase Disulfation Procedure

The sulfate ester-containing peptide is prepared by disulfation of the side-chain of Tyr and Thr using (PAS) or pyridine sulfur trioxide complex (PS). A typical sulfation is carried out as follows: PAS (218 mg; 1 mmol, 38 equiv.) or PS (162 mg; 1 mmole, 38 equiv) is dissolved in 20 mL of dry Pyridine and 100 mg of peptide-resin ( 0.0268 mmole of peptide) is added. The suspension is shaken 4 hours at 45°C. then filtered on a sintered glass funnel and successively washed with pyridine, DMF and MeOH. The resin is dried overnight in vacuo.

3. Ammonolysis of the Peptide-resin

The dried peptide-resin is placed in a Wheaton pressure bottle (250 mL capacity). The container is purged with anhydrous ammonia, cooled to −78° C using a dry ice-acetone bath, and ammonia ( 20 mL) condensed into the reaction vessel. The bottle is tightly capped, the bath is removed and the resin stirred overnight at room temperature. At the end of the reaction, the pressure bottle is cooled to −78°C. before opening and the ammonia is evaporated quickly by immersing the vessel in a water bath. The peptide is extracted with MeOH (3×15 mL). The solvent is evaporated and the crude Ac-Tyr(SO$_3$H)-Met-Gly-Trp-Met-Thr (SO$_3$H)-N-methyl-Phe-NH$_2$ is ready for purification. From 100 mg of sulfated peptide resin, 19.3 mg of crude material was obtained after ammonolysis. Analysis by hplc indicated that the sample contained 8.0 mg of disulfated peptide for an overall yield of 57%.

4. Purification and Characterization of the Crude Peptide

The crude peptide was dissolved in 0.7 mL of glacial acetic and 0.7 mL of water was added. The cloudy solution was filtered through a 0.45 µType HA millipore filter. The filtrate was applied onto an ES Industries $C_{18}$ 10μ column (0.9×30 cm). A linear gradient of (A) 0.01M ammonium acetate and (B) acetonitrile [10–40% (B)]60 min; flow rate 8 mL/min with detection at 280 nm. Fractions were pooled and lyophilized to give 2.8 mg (20% overall yield) of pure material Amino acid analysis: Ultraviolet spectrum: λmax 272 and 278 nm (0.1N NaOH), Infrared spectrum: —$OSO_3H$ with peaks of 1252–1232 and 1048 $cm^1$ (KBr), NMR (400 MHz): Confirms $Tyr^{27}$ ($SO_3H$) and N-methyl-Phe [$d_6$DMSO].

The homogeneity of this material was determined by analytical HPLC using μBondapak $C_8$, 10μ column (0.30×30 cm) using a (A) $H_2O$ (0.125% TFA) (B) acetonitrile containing 0.015% TFA in a linear gradient (20 to 55% (B) in 25 min) with a flow rate of 2.5 mL/min and detection at 215 nm.

The synthesis of CCK where Nle is substituted for Met may be accomplished according to this methodology except that Nle is substituted for Met in the solid phase synthesis procedure.

While the invention has been described in connection with the preferred embodiment, it is not intended to limit the scope of the invention to the particular form set forth, but, on the contrary, it is intended to cover such alternatives, modifications, and equivalents as may be included within the spirit and scope of the invention as defined by the appended claims.

I claim:

1. A method for the solid phase synthesis of multi-sulfated peptides comprising coupling side-chain unprotected hydroxyamino acids to the peptide chain utilizing benzotriazol-1-yl-oxy-tris-(dimethy)-oxy-tris-(dimethyl)-phosphonium hexafluorophosphate (BOP) as a coupling reagent.

2. The method of claim 1 wherein the side-chain unprotected amino acids are t-butyloxycarbonyl hydroxyamino acids.

3. The method of claim 2 wherein three equivalents of benzotriazol-1-yl-oxy-tris-(dimethyl)-phosphonium hexafluorophosphate and three equivalents of t-butyloxycarbonyl hydroxyamino acids are used in a single coupling.

4. The method of claim 3 wherein the multisulfated peptides contain tyrosine.

5. The method of claim 4 wherein the peptide is cholecystokinin or an analog of cholecystokinin (CCK).

6. The method of claim 5 wherein the CCK analog is a peptide of the formula

X—(R)$_n$—Tyr(SO$_3$H)—R$_1$—R$_2$—R$_3$—R$_4$—R$_5$—N-methyl-Phe—Y

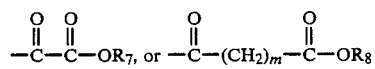

R = Asp, Aeg
$R_1$ = Met, Nle, Leu, or 0 (Zero)
$R_2$ = Gly, Ala, D-Ala, or β-Ala
$R_3$ = Trp, Trp (For)
$R_4$ = Met, Nle, Nva, Pro
$R_5$ = Thr(SO$_3$H), Ser(SO$_3$H), or Hyp(SO$_3$H)
$R_6$ = H, $C_{1-3}$alkyl
$R_7$ = $R_8$ = H, $C_{1-3}$alkyl, or $C_{1-3}$haloalkyl
$R_8$ = H, $C_{1-3}$alkyl
Y = OR$_8$ or NR$_9$R$_{10}$
$R_9$ = H, $C_{1-3}$alkyl
$R_{10}$ = H, $C_{1-3}$alkyl
n = 0 or 1
m = 1–14

7. The method of claim 6 wherein the CCK analog is a peptide of the formula

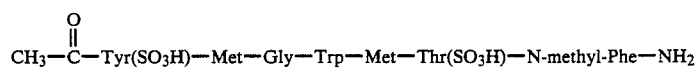

8. The method of claim 6 wherein the CCK analog is a peptide of the formula

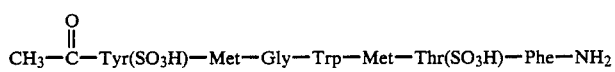

9. The method of claim 6 wherein the CCK analog is a peptide of the formula

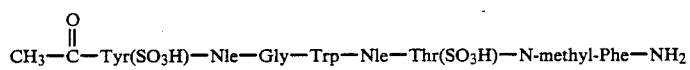

10. A method for the solid phase synthesis of multi-sulfated peptides comprising the steps of:
(a) preparing the α-amino acid protected [4—(oxymethyl) phenylacetamidomethyl] polystyrene (O—CH$_2$-PAM) resin
(b) sequentially adding side-chain unprotected t-butyloxycarbonyl hydroxyamino acids to the peptide chain utilizing BOP as the coupling reagent
(c) reacting the amino acid hydroxyl groups with a sulfating agent at 40–50°C. to yield the sulfate esters
(d) cleaving the multi-sulfated peptide with a nucleophilic agent
(e) Purifying the multi-sulfated peptide by HPLC.

11. The method of claim 10 wherein three equivalents of BOP and three equivalents of t-butyloxycarbonyl hydroxyamino acids are used in a single coupling.

12. The method of claim 11 wherein the sulfating agent is pyridinium acetyl sulfate (PAS) or pyridine sulfur trioxide (PS) complex.

13. The method of claim 12 wherein the sulfating agent is reacted at approximately 42–48°C.

14. The method of claim 13 wherein the sulfating agent is reacted at approximately 45°C.

15. The method of claim 14 wherein the nucleophilic agent is selected from the group consisting of ammonia, amines, or hydrazine.

16. The method of claim 15 wherein the peptide synthesized is CCK or an analog of CCK.

17. The method of claim 16 wherein the CCK analog is of the formula

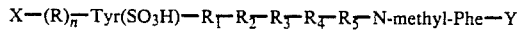

wherein $X = -\overset{O}{\underset{\|}{C}}-R_6,\ -\overset{O}{\underset{\|}{C}}-OR_6,\ -\overset{O}{\underset{\|}{C}}-(CH_2)_m-CH_3,$ $-\overset{O}{\underset{\|}{C}}-\overset{O}{\underset{\|}{C}}-OR_7,\ \text{or}\ -\overset{O}{\underset{\|}{C}}-(CH_2)_m-\overset{O}{\underset{\|}{C}}-OR_8$ R = Asp, Aeg
$R_1$ = Met, Nle, Leu, or 0 (Zero)

-continued
$R_2$ = Gly, Ala, D-Ala, or β-Ala
$R_3$ = Trp, Trp (For)
$R_4$ = Met, Nle, Nva, Pro
$R_5$ = Thr(SO$_3$H), Ser(SO$_3$H), or Hyp(SO$_3$H)
$R_6$ = H, C$_{1-3}$alkyl
$R_7$ = $R_8$ = H, C$_{1-3}$alkyl, or C$_{1-3}$haloalkyl
$R_8$ = H, C$_{1-3}$alkyl
Y = OR$_8$ or NR$_9$R$_{10}$
$R_9$ = H, C$_{1-3}$alkyl
$R_{10}$ = H, C$_{1-3}$alkyl
n = 0 or 1
m = 1-14

18. The method of claim 17 wherein the peptide is of the formula

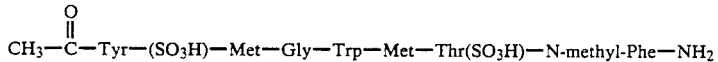

19. The method of claim 18 wherein the peptide is of the formula

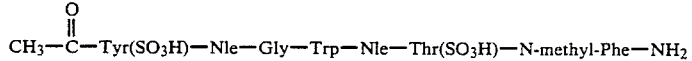

* * * * *